US008231643B2

(12) United States Patent  (10) Patent No.: US 8,231,643 B2
Davis  (45) Date of Patent: Jul. 31, 2012

(54) UNIVERSAL LIMBAL RELAXING INCISION GUIDE

(76) Inventor: Andrew Davis, Bellevue, WA (US)

( * ) Notice: Subject to any disclaimer, the term of this patent is extended or adjusted under 35 U.S.C. 154(b) by 285 days.

(21) Appl. No.: 12/465,439

(22) Filed: May 13, 2009

(65) Prior Publication Data

US 2009/0287232 A1  Nov. 19, 2009

Related U.S. Application Data

(60) Provisional application No. 61/127,444, filed on May 13, 2008.

(51) Int. Cl.
A61F 9/00 (2006.01)
(52) U.S. Cl. ........................ 606/166; 623/6.12
(58) Field of Classification Search .............. 606/166, 606/167, 161, 107, 4, 5; 623/6.12; 600/587; 33/512; 128/205.23; 209/204, 212, 217, 209/234
See application file for complete search history.

(56) References Cited

U.S. PATENT DOCUMENTS

| | | | |
|---|---|---|---|
| 4,417,579 A | 11/1983 | Soloviev et al. | |
| 4,476,862 A | 10/1984 | Pao | |
| 4,705,035 A | 11/1987 | Givens | |
| 4,713,535 A | 12/1987 | Rhoades | |
| 4,739,761 A * | 4/1988 | Grandon | 606/166 |
| 5,013,319 A | 5/1991 | Davis | |
| 5,104,214 A | 4/1992 | Sims | |
| 5,314,439 A | 5/1994 | Sugita | |
| 6,045,562 A * | 4/2000 | Amano et al. | 606/166 |
| 6,217,596 B1 | 4/2001 | Farah | |
| 6,527,788 B1 * | 3/2003 | Hellenkamp | 606/166 |
| 6,673,069 B1 | 1/2004 | Hood | |
| 6,776,756 B2 | 8/2004 | Feldon et al. | |
| 2002/0082628 A1 | 6/2002 | Hellenkamp | |
| 2003/0216763 A1 | 11/2003 | Patel | |
| 2005/0096639 A1 | 5/2005 | Slatkine et al. | |
| 2005/0203554 A1 | 9/2005 | Dykes | |
| 2007/0121067 A1 | 5/2007 | Davis | |
| 2008/0228210 A1 | 9/2008 | Davis | |
| 2009/0254108 A1 | 10/2009 | Davis | |

FOREIGN PATENT DOCUMENTS

JP  07231875  9/1995
* cited by examiner

Primary Examiner — Ryan Severson
Assistant Examiner — Tin Nguyen
(74) Attorney, Agent, or Firm — Lowe Graham Jones PLLC

(57) ABSTRACT

An apparatus and method for accurately making a limbal relaxing incision. An example universal limbal relaxing guide (ULRIG) includes an inner rotating ring, a measurement gauge, a base unit and bumpers. The inner rotating ring and measurement gauge rotate concentrically relative to the base unit. The inner ring guides a keratome along an arc of constant radius. The measurement gauge enables the user to select the length of the arc and the bumpers prevent the keratome from overshooting the desired incision length. Because the thin degree ring rotates relative to the base unit, the example ULRIG can be used with more than one style of keratome. Multiple marks on a pointing bumper enable the user to adjust the resultant incision length for the cornea size of an individual patient.

8 Claims, 6 Drawing Sheets

US 8,231,643 B2

UNIVERSAL LIMBAL RELAXING INCISION GUIDE

PRIORITY CLAIM

This application claims the benefit of U.S. Provisional Application Ser. No. 61/127,444 filed May 13, 2008; contents of which are incorporated herein.

FIELD OF THE INVENTION

This invention relates generally to ophthalmic instrumentation and, more specifically, to an ophthalmic instrument to assist in making an accurate limbal relaxing incision (LRI).

BACKGROUND OF THE INVENTION

A Limbal Relaxing Incision (LRI) is a deep circumferential incision made in the peripheral margin of the cornea (the limbus) to reduce the astigmatic component of a patient's refractive error. The incisions are most often performed at the time of cataract surgery, but can also be performed as a separate procedure.

Accurately making a limbal relaxing incision can be technically challenging. One challenge is making an incision that is both smooth and at a proper angle. The difficulty is that a surgeon must incise an arc concentric about an axis of the eye over an angle of 90 degrees or more while maintaining the tangential orientation and angle of inclination of the keratome (the scalpel which performs the incision to a preset depth) as it travels around the limbus. A second challenge is ensuring the incision is at precisely the correct length, since the degree of astigmatic reduction is determined precisely by the length of the incision. The difficulty here is that due to differences in the corneal diameter from patient to patient, the same number of degrees of arc can result in significant differences in the absolute length of the incision.

Corneal markers are available to surgeons to pre-mark the cornea in order to assist in achieving an accurate incision. One type marks radial lines on the cornea at 40 degrees and 80 degrees, but the surgeon must still estimate the actual incision endpoints for an individual patient. Other corneal markers mark a circumferential line, but the surgeon must still estimate the circumferential length to accommodate for the individual patient's cornea size.

Commercially, Mastel Instruments offers a Mendez gauge-style ring that serves as a guide for making limbal relaxing incisions. However, even with the gauge the surgeon still must estimate incision length. With the gauge there is also a risk of overshooting the desired incision length since friction can develop between the guide and the keratome, causing the guide to stick. Another commercial provider, Duckworth and Kent, makes a similar ring gauge of different diameters, but this gauge also does not eliminate the risk of overshooting the desired incision length.

SUMMARY OF THE INVENTION

The present invention provides an apparatus and method for accurately making a limbal relaxing incision. An example universal limbal relaxing incision guide (ULRIG) includes a base unit, a rotating ring, a measurement or thin degree gauge, a bridging bumper, a pointing bumper, a first and second precision indicator marks and a handle.

The base unit, rotating ring and measurement gauge are preferably rigid bodies positioned concentrically with respect to one another. The measurement gauge provides a graduated scale for quantifying the length of a limbal relaxing incision. The base unit provides a reference path of constant radius for the keratome to follow and the bridging bumper a reference point for the start of an incision. Rotation of the rotating ring moves the pointing bumper along the measurement gauge, thereby indicating the length of the incision for a keratome tracing the base unit as it follows the rotating ring from the bridging bumper to the pointing bumper.

First and second precision indicator marks on the base unit and rotating ring, respectively, assist with accurate placement of the ULRIG relative to the astigmatic axis of the patient's cornea. Multiple reference points on the pointing bumper allow for adjustment of the incision length due to variation in cornea size from patient to patient. Adjustment of the measurement gauge relative to the bridging bumper allows the ULRIG to accommodate various keratome. The bumpers reduce the risk of making an incision that overshoots the desired incision length.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
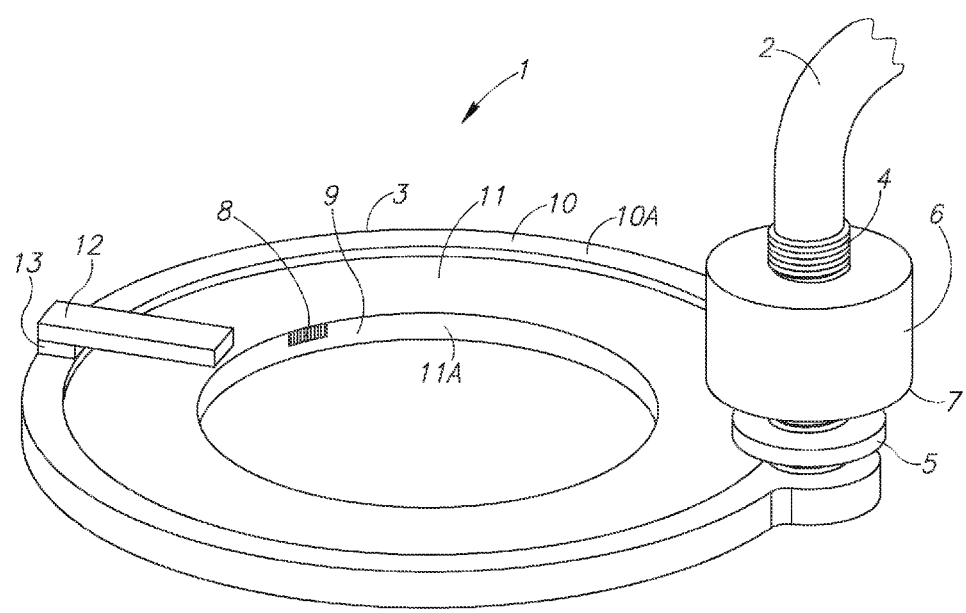
FIG. 1 shows a perspective view of a base unit and handle of an embodiment of the present invention Universal Limbal Relaxing Incision Guide (ULRIG)

FIG. 1 shows a preferred embodiment of the present invention, including a base unit 1, including a handle 2 and a base ring 3. The handle 2 includes a threaded end 4 that may attach the handle 2 to the base ring 3. Alternatively, the handle 2 may be attached to the based unit 1 or a third member (not shown) that is used to provide support to the apparatus. The threaded end 4 preferably engages a small inner nut 5, and above it, a large outer nut 6.

Figure 2:
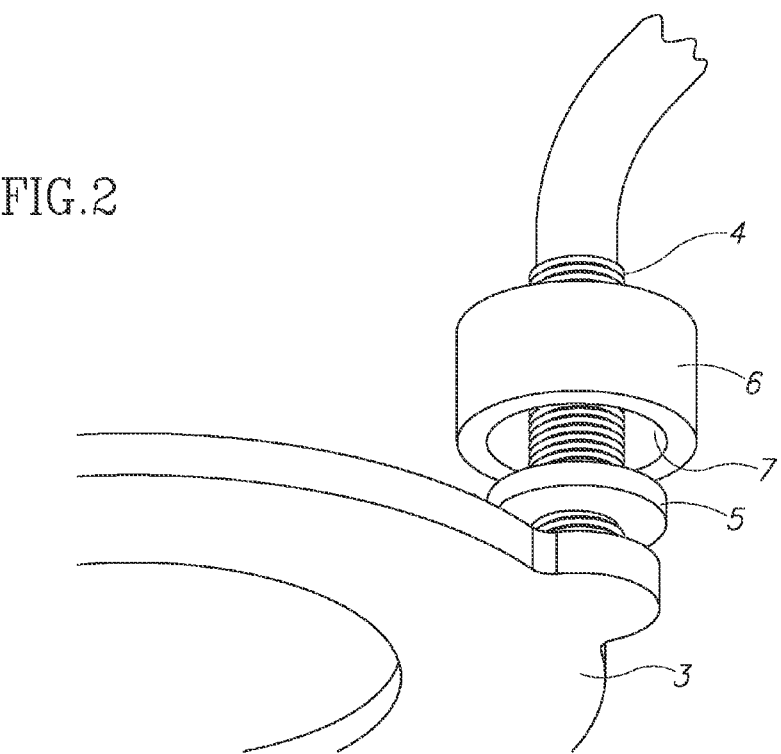
FIG. 2 shows a perspective view of an inner and outer nut of an embodiment of the present invention ULRIG.

FIG. 2 shows the outer nut 6, which preferably includes a hollow lower end 7 that allows the lower end to fit over the small inner nut 5 without engaging the smaller inner nut as the large outer nut 6 is threaded downward on the threaded end 4 of the handle 2. This is a means for securing the position of the base ring 3 with respect to the base unit 1 to prevent undesirable rotation of the apparatus once proper alignment is achieved. Alternative means of securing the apparatus are contemplated; for example, a locking clip, a pass-through bolt, or the frictional relationship between the base unit 1 and base ring 3.

Referring again to FIG. 1, the base 1 preferably further includes a base ring 9 having a raised outer portion 10 and a recessed lower portion 11. An inside face 11A of the recessed lower portion 11 of the base ring 9 includes a first precision indicator mark 8 that in this embodiment identifies this point on the circumference of the base ring 9 as the "10-degree" mark. An elevating element 13 is fixed to a top face 10A of the raised outer portion 10 of the base ring 9. A bridging bumper 12 is fixed to the elevating element 13. The bridging bumper 12 extends from the elevating element 13 over the recessed lower portion 11 of the base ring 3 to approximately the inside face 11A of the recessed lower portion 11 of the base ring 9.

Figure 3:
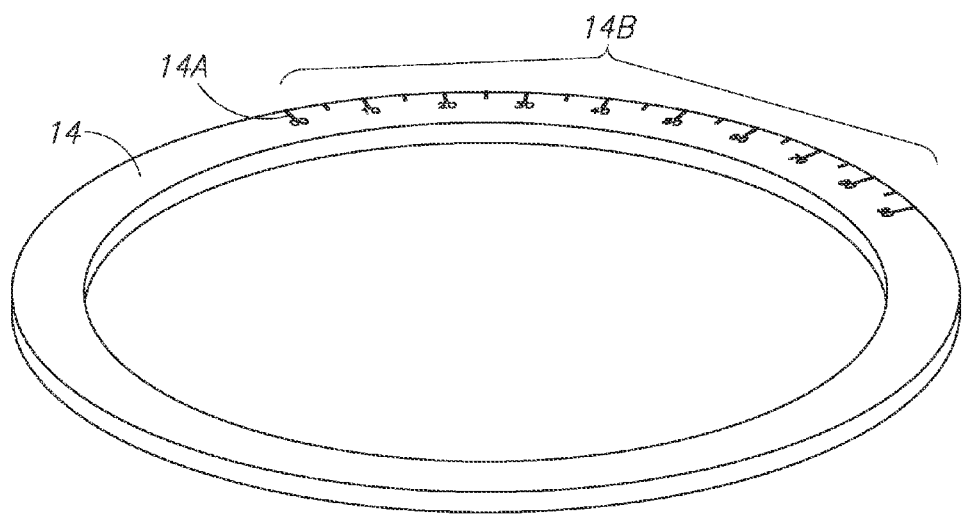
FIG. 3 shows a perspective view of a measurement gauge of an embodiment of the present invention ULRIG.

FIG. 3 shows an exemplary embodiment of a measurement gauge 14. The measurement gauge includes a zero point 14A and a series of graduation marks 14B corresponding to degrees in an arc.

Figure 4:
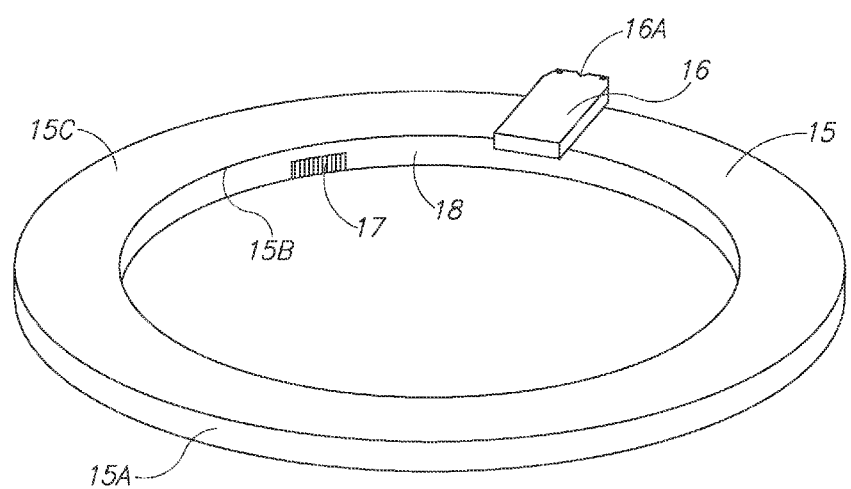
FIG. 4 shows a perspective view of an inner rotating ring of an embodiment of the present invention ULRIG.

FIG. 4 shows an inner rotating ring 15 including an outer face 15A, an inner edge 15B, a top face 15C and an inner face 18. A pointing bumper 16 having a central mark 16A is fixed to the top face 15C of the inner rotating ring 15. A second precision indicator mark 17 is located on the inner face 18 of the inner rotating ring 15 that in this embodiment identifies this point on the circumference of the inner rotating ring as the "10-degree" mark.

Figure 5:
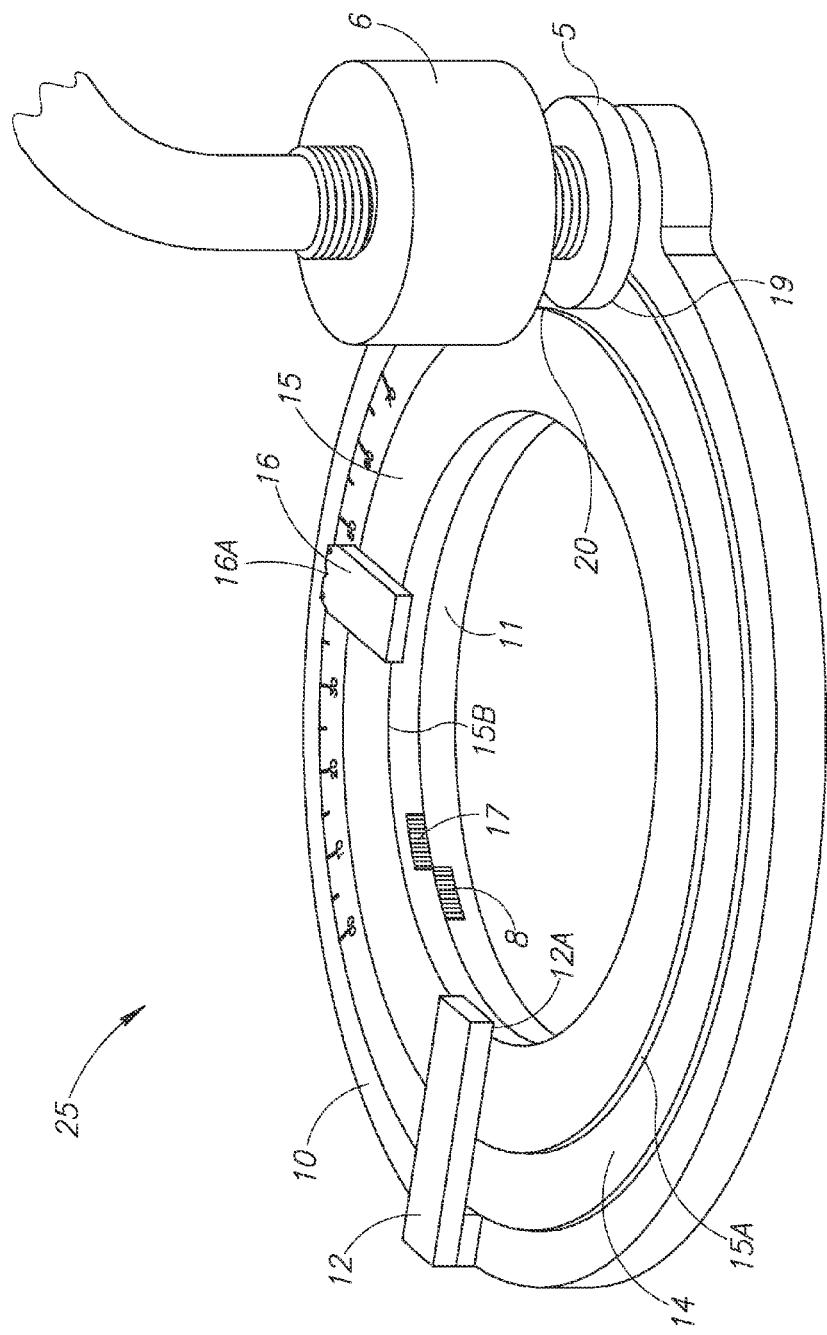
FIG. 5 shows a perspective view of an assembled embodiment of the present invention ULRIG.

FIG. 5 shows a preferred embodiment of the present invention ULRIG 25 fully assembled, including the base unit 1, the measurement gauge 14 and the inner rotating ring 15. In this embodiment the inner rotating ring 15 is sized to fit concentrically within the raised portion 10 of the base ring 3 and rest on top of the recessed portion 11 of the base ring 3. The inner rotating ring 15 passes underneath the portion of the bridging bumper 12 that overhangs the recessed portion 11 of the base ring 3.

In this embodiment the measurement gauge 14 is sized to fit concentrically around the outside of the inner rotating ring 15 and within the inside diameter of the raised portion 10 of the base ring 3. The inside diameter of the measurement gauge 14 is slightly greater than the outside diameter of the inner rotating ring 15 so that the measurement gauge 14 snugly fits around the inner rotating ring 15 but still allows the inner rotation ring and the measurement gauge to rotate freely of one another. The measurement gauge 14 preferably passes underneath the bridging bumper 12. Furthermore, the inside diameter of the raised portion 10 of the base ring 3 is preferably slightly greater than the outside diameter of the measurement gauge 14 so that the measurement gauge snugly fits within the raised portion 10 of the base ring 3 while allowing the measurement gauge 14 to rotate freely of the base ring 3.

When assembled, the elevation of the measurement gauge 14 is preferably slightly below that of the inner rotating ring 15. The radius of the inner nut 5 and the nut's position relative to the base unit 3 cooperate so that by turning the inner nut 5 down the threaded end 4 of the handle 2, the inner nut 5 clamps the measurement gauge 14 at a first clamping point 19 between the inner nut and the base ring 3. This procedure locks the measurement gauge 14 in place relative to the base unit 3. The radius of the inner nut 5 and the nut's position relative to the base unit 3 preferably are configured to cooperate so that the inner nut 5 cannot reach the inner rotating ring 15, therefore rotation of the inner rotating ring 15 is unimpeded by the procedure of clamping the measurement gauge 14 to the base unit 3.

The radius of the outer nut 6 and the nut's position relative to the base unit 3 preferably cooperate so that by turning the outer nut 6 down the threaded end 4 of the handle 2, the outer nut 6 clamps the inner rotating ring 15 at second clamping point 20, between the outer nut 6 and the base ring 3. In this embodiment, the procedure locks the inner rotating ring 15 in place relative to the base unit 3. The higher elevation of the inner rotating ring 15 relative to the measurement gauge 14 prevents the outer nut 6 from contacting the measurement gauge and provides for rotation of the measurement gauge 14 substantially unimpeded by the procedure of clamping the inner rotating ring 15 to the base unit 3.

Figure 6:
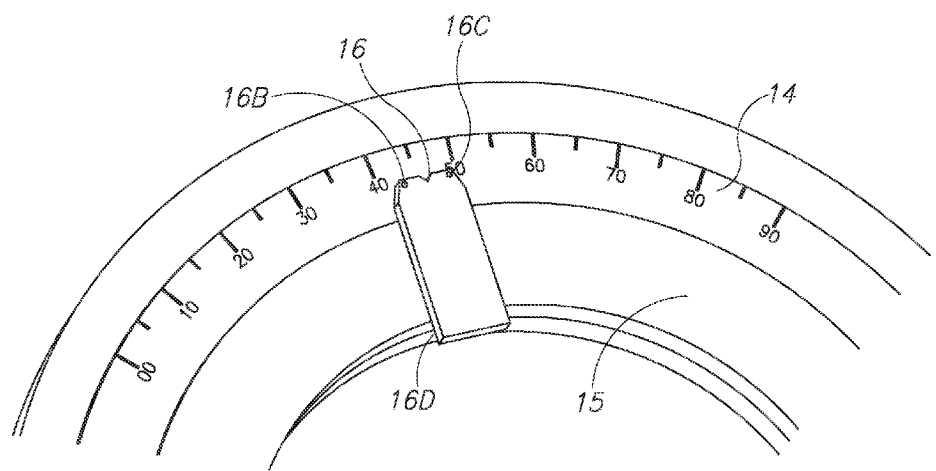
FIG. 6 shows a close-up perspective view of the measurement gauge and a pointing bumper of an embodiment of the present invention ULRIG.

FIG. 6 illustrates how the preferred invention accommodates for patients having different size cornea. For patients having a larger than average cornea, the surgeon chooses an alternative mark 16B or 16C in place of the central mark 16A. For example, for patients having a cornea of smaller than average size, the surgeon chooses the lower value alternative mark 16B as read by the measurement gauge 14.

Figure 7:
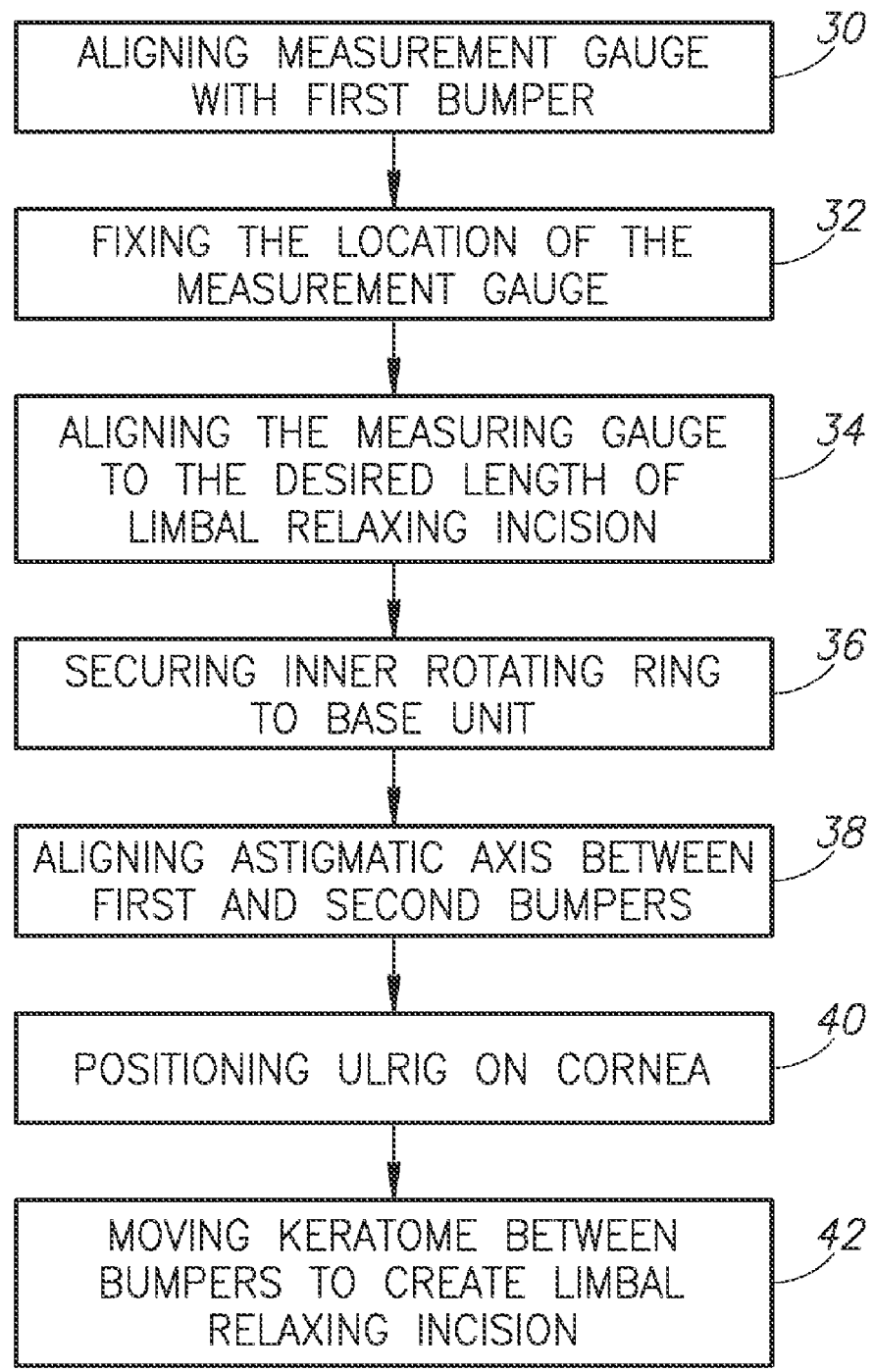
FIG. 7 shows a flow diagram of an example method for making a limbal relaxing incision with the assistance of an embodiment of the present invention ULRIG.

FIG. 7 discloses a flow diagram of an example method for making a guided limbal relaxing incision using, for example, the ULRIG 25 described with reference to FIG. 5. At a block 30, the measurement gauge 14 is aligned with the first bumper. This is preferably done by aligning a zero point on the measurement gauge with a central mark on the bridge bumper affixed to an inner rotating ring 15 held within the base unit 3 by rotating the inner rotating ring. Alternative methods of alignment using other than a zero point on the measurement gauge or a central mark on the first bumper are contemplated. This facilitates using a keratome between the bridge bumper 12 and the pointing bumper 16 while the keratome is positioned on the inner edge 15B of the inner rotating ring 15.

At a block 32 the location of the measurement gauge 14 is fixed with respect to the base unit. In the preferred embodiment, this is accomplished by lowering the inner nut 5 on the threaded handle end 4 to clamp the measurement gauge 14 to the base unit 3. Blocks 30-32 do not need to be repeated for each incision if the operator uses the ULRIG with the same keratome.

At a block 34, the inner rotating ring 15 is rotated to align it with the measurement gauge corresponding to the desired length of the limbal relaxing incision. In the preferred embodiment, this is accomplished by rotating the inner ring to the desired incision length (for example, 45 degrees) as designated by the position of the central mark 16A on the degree gauge 14. At a block 36, the inner rotating ring 15 is secured to the base unit 3. In the preferred embodiment, this is accomplished by lowering the larger outer nut 6 on the threaded handle 4 to clamp the inner rotating ring to the base unit. Next at a block 38, the patient's astigmatic axis is aligned with a midpoint between the bridge bumper 12 and the pointing bumper 16. In the preferred embodiment, the patient's astigmatic axis is aligned with the midpoint between first and second precision indicator marks located on the rotating ring or the base unit or both.

At block 40, the ULRIG 25 is placed on a patient's cornea. At a block 42, the keratome is moved along the inner rotating ring between the bridge bumper 12 and the pointing bumper 16 to create the limbal relaxing incision. This method provides a guided limbal relaxing incision of accurate position and desired length with minimal overshoot. In the preferred embodiment, this is accomplished by rotating the inner rotating ring to move the keratome between the bumpers. In one embodiment, a slight protrusion of the bridging bumper 12 and the pointing bumper 16 equal to approximately 0.5 mm assists in aligning the incision, since the keratome is at an angle tangential to the cornea while the keratome rests on the inner rim 15B of the inner rotating ring 15. As a result, in this embodiment the incision may be located about 0.5 mm inside the inner diameter 9 of the base ring 11.

While the preferred embodiment of the invention has been illustrated and described, as noted above, many changes can be made without departing from the spirit and scope of the invention. For example, the precision indicators on the inner faces can be various sizes shapes and colors, all to assist in designating the mid-position between the two bumpers. A multitude of methods for securing the thin degree ring to the base are also envisioned. Additionally, the measurement gauge could be integrated with the base, and therefore not be rotationally adjustable if the ULRIG is manufactured for dedicated use with a particular keratome. In this case the degree gauge could simply be printed on the base ring. In another embodiment, a separate triangular-shaped gauge instrument could be used to set the distance between the bumpers. In addition, the gauge could show gradient marks in units of millimeters, rather than degrees, or in both units simultaneously. Accordingly, the scope of the invention is not limited by the disclosure of the preferred embodiment. Instead, the invention should be determined entirely by reference to the claims that follow. claimed are defined as follows:

The embodiments of the invention in which an exclusive property or privilege is:

1. An apparatus, comprising:
   a first member having a center opening and a surface of a constant radius;
   a second member concentric with the surface of the first member, the first and second members rotatable with respect to each other;
   a measurement gauge concentric with the surface of at least one of the first and second members;
   a first bumper fixed to the first member and extending toward the center opening of the first member and a second bumper fixed to the second member and extending toward a center opening of the second member, wherein
      at least one of the first and second bumpers is alignable with respect to the measurement gauge; and
      the first and second bumpers are configured to guide a keratome in the creation of a limbal relaxing incision in the peripheral margin of a patient's cornea; and
   a handle providing support for at least one of the first and second members.

2. The apparatus of claim 1, further comprising an indicator mark on at least one of the first and second members to facilitate alignment of at least one of the first and second bumpers with respect to the measurement gauge.

3. The apparatus of claim 1, further comprising an indicator mark on at least one of the first and second bumpers to facilitate alignment of at least one of the first and second bumpers with respect to the measurement gauge.

4. The apparatus of claim 1, wherein the handle is attached to at least one of the first and second members.

5. The apparatus of claim 1, further comprising a means for securing the position of the first member in relation to the second member.

6. The apparatus of claim 1, wherein the keratome is guided in the creation of a limbal relaxing incision in the peripheral margin of a patient's cornea by rotation of at least one of the first or second members to urge at least one of the first or second bumpers towards the other bumper.

7. An apparatus, comprising:
   a base unit having a center opening and a surface of a constant radius;
   a rotating ring concentric with the surface of the base unit;
   a measurement gauge concentric with the surface of the base unit;
   a bridging bumper fixed to the base unit and extending toward the center opening of the base unit and a pointing bumper fixed to the rotating ring and extending toward the center opening of the base unit, wherein the bridging and pointing bumpers are configured to guide a keratome in the creation of a limbal relaxing incision in the peripheral margin of a patient's cornea;
   a first indicator mark on the base unit;
   a second indicator mark on the rotating ring; and
   a handle attached to the base unit.

8. The apparatus of claim 7, wherein the keratome is guided in the creation of a limbal relaxing incision in the peripheral margin of a patient's cornea by rotation of at least one of the base unit or rotating ring to urge at least one of the bridging or pointing bumpers towards the other bumper.

\* \* \* \* \*